United States Patent
Bonnefous

(10) Patent No.: US 7,717,852 B2
(45) Date of Patent: May 18, 2010

(54) METHOD AND DEVICE FOR DETERMINING THE MOTION VECTOR TISSUES IN A BIOLOGICAL MEDIUM

(75) Inventor: Odile Mattheiu Bonnefous, Rueil-Malmaison (FR)

(73) Assignee: Koninklijke Philips Electronics N.V., Eindhoven (NL)

(*) Notice: Subject to any disclaimer, the term of this patent is extended or adjusted under 35 U.S.C. 154(b) by 478 days.

(21) Appl. No.: 11/814,087

(22) PCT Filed: Jan. 18, 2006

(86) PCT No.: PCT/IB2006/050189

§ 371 (c)(1), (2), (4) Date: Jul. 17, 2007

(87) PCT Pub. No.: WO2006/077541

PCT Pub. Date: Jul. 27, 2006

(65) Prior Publication Data

US 2008/0167554 A1 Jul. 10, 2008

(51) Int. Cl.
*A61B 8/00* (2006.01)
*G06K 9/00* (2006.01)

(52) U.S. Cl. .................... 600/450; 600/441; 600/443; 128/916; 382/128

(58) Field of Classification Search ............ 600/441, 600/443, 450; 382/128; 128/916
See application file for complete search history.

(56) References Cited

U.S. PATENT DOCUMENTS

| 4,911,014 A | * | 3/1990 | Lund et al. ............ 73/602 |
| 5,910,119 A | | 6/1999 | Lin |
| 6,371,913 B2 | | 4/2002 | Pang |
| 6,527,717 B1 | | 3/2003 | Jackson |
| 6,589,179 B2 | | 7/2003 | Criton |
| 6,679,847 B1 | | 1/2004 | Robinson |

OTHER PUBLICATIONS

Criton A. et al "Real Time Vector Doppler for Tissue Motion" IEEE Ultrasonics Symposium 2002.

* cited by examiner

*Primary Examiner*—Eric F Winakur
*Assistant Examiner*—Michael T Rozanski

(57) ABSTRACT

The invention relates to a method of determining the motion vector of tissues in a biological medium. This method comprises the steps of: —acquiring a sequence of echographical images at a given repetition rate, —digitalising said echographical images and storing the so-digitalised images, —defining a digital pseudo echographical pulse, —effecting in a plurality of directions a convolution of said digital pseudo echographical pulse with said digitalised images and deducing therefrom at each point of said medium a plurality of pseudo echographical signals associated with said plurality of directions, —determining an estimate over said plurality of directions of the phase shift between two successive pseudo echographical signals and deducing therefrom the magnitude and the direction of said motion vector.

9 Claims, 4 Drawing Sheets

METHOD AND DEVICE FOR DETERMINING THE MOTION VECTOR TISSUES IN A BIOLOGICAL MEDIUM

FIELD OF THE INVENTION

The present invention relates to a method and a device for determining the motion vector of tissues in a biological medium.

The invention is particularly relevant to the measurement of 3D vectorial tissue motion in a biological medium, mainly for cardiac application.

BACKGROUND OF THE INVENTION

Tissue motion is usually measured by use of a method known as Tissue Doppler Imaging consisting in recording the successive responses of a medium to ultrasonic excitations generated at a given repetition rate, the phase shift between two successive response signals being directly related to the motion vector component along the excitation beam axis. However, this method only enables the measurement of the motion vector component along this axis.

On the other hand, a classic 3D echography method is not likely to provide a satisfactory solution, because it is not practically possible to record simultaneously several orientations which could allow the reconstruction of the overall motion vector due to the required complexity and high cost it involves and/or accessibility constraints.

SUMMARY OF THE INVENTION

It is an object of the invention to provide a method which could lead to the determination of the three components of the tissue motion vector and which would be simpler and cheaper to carry out than 3D echographical data processing.

To this end, the invention proposes a method of determining the motion vector of tissues in a biological medium, said method comprising the steps of:

acquiring a sequence of echographical images at a given repetition rate, digitalising said echographical images and storing the so-digitalised images, defining a digital pseudo echographical pulse, effecting in a plurality of directions a convolution of said digital pseudo echographical pulse with said digitalised images and deducing therefrom at each point of said medium a plurality of pseudo echographical signals associated with said plurality of directions, determining an estimate over said plurality of directions of the phase shift between two successive pseudo echographical signals and deducing therefrom the magnitude and the direction of said motion vector.

Thus, in a first stage, the echographical images are collected in a usual way making use of a 3D acquisition probe, and in a second stage, instead of processing said images by means of a complex and expensive 3D method, a Tissue Doppler Imaging method is simulated using the digitalised echographical images as the actual medium, leading to the determination of the components of the motion vector in any direction and not only one direction as is usually the case with this 3D method.

In that context, the expression "digital pseudo echographical pulse" is to be interpreted as a simulation in a digitalised way of the ultrasonic pulse which would be used in an actual Tissue Doppler Imaging experiment.

Since the second stage of the method in accordance with the invention is only a digital simulation of a Tissue Doppler Imaging method applied to digital images, one can readily understand that the method according to the invention may be simple, fast and used without accessibility constraints.

Accordingly, the invention proposes a device for determining the motion vector of tissues in a biological medium, said device comprising:

means for acquiring a sequence of echographical images at a given repetition rate, means for digitalising said echographical images and storing the so-digitalised images, means for effecting in a plurality of directions a convolution of a digital pseudo echographical pulse with said digitalised images and means for deducing therefrom at each point of said medium a plurality of pseudo echographical signals associated with said plurality of directions, means for determining an estimate over said plurality of directions of the phase shift between two successive pseudo echographical signals and deducing therefrom the magnitude and the direction of said motion vector.

BRIEF DESCRIPTION OF THE DRAWINGS

The invention will now be described in more detail, by way of example, with reference to the accompanying drawings in which.

DETAILED DESCRIPTION OF THE INVENTION

Figure 1:
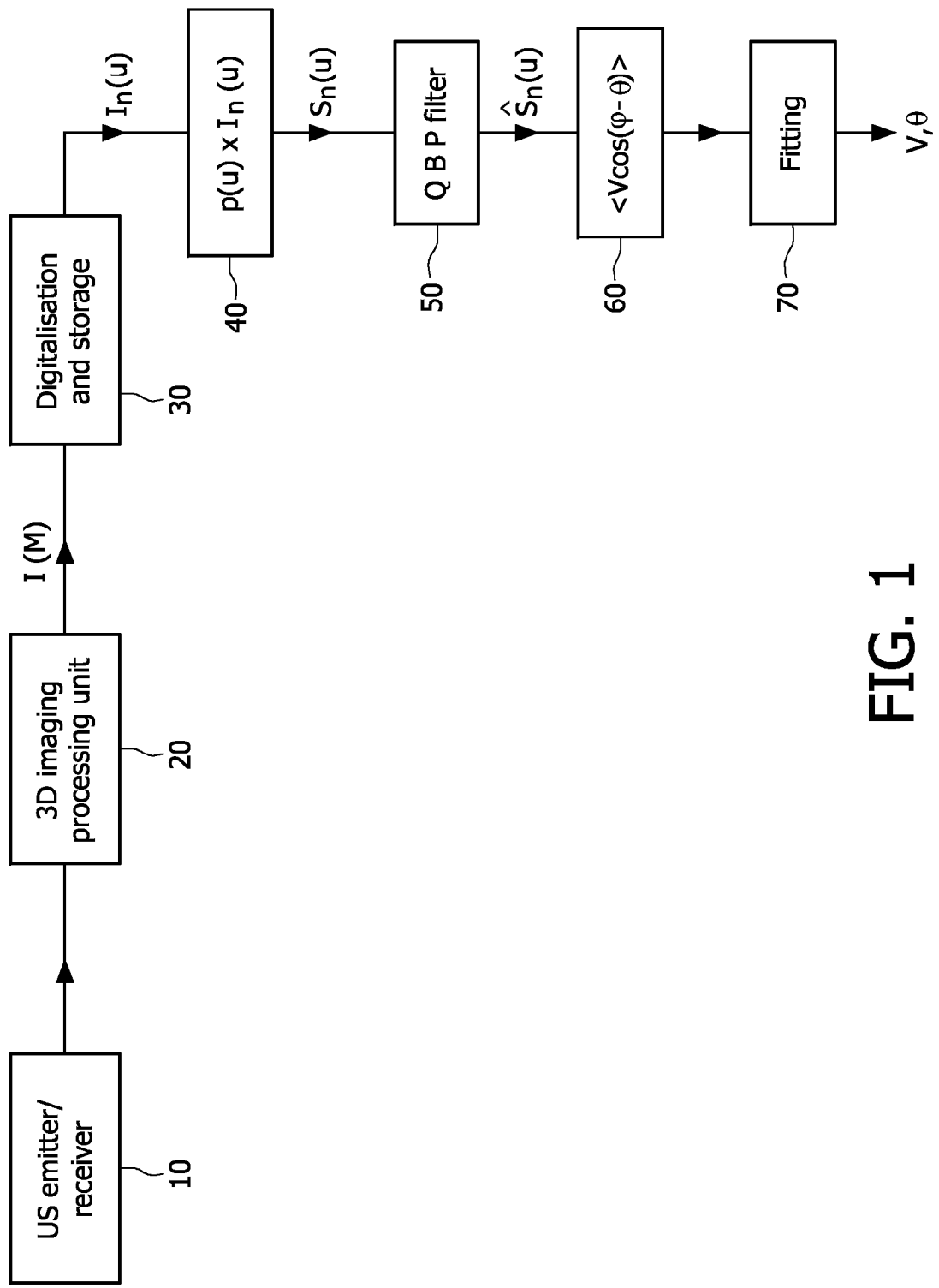
FIG. 1 is a block diagram of a device for implementing the method in accordance with the invention.
Figure 2:
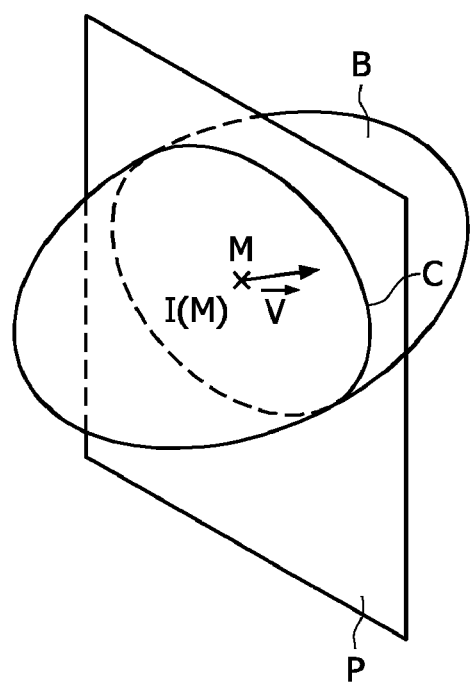
FIG. 2 is a perspective view of a volume containing a biological medium.

FIG. 1 shows a block diagram of a device designed to carry out a method of determining the motion vector of tissues in a biological medium. Such a medium, a cardiac muscle for example, is represented in FIG. 2 by reference B. Said medium B is made up of tissues the motion of which is intended to be determined thanks to the method in accordance with the invention.

In other words, if M is a current point of the tissues of medium B and V is the motion vector attached to point M during the motion of said tissues, heart beats in this example, the purpose of the invention is to determine in a simple and cheap way the three components of vector V.

In order to meet that purpose, 3D echographical images of medium B are acquired at a repetition rate $f_r$ by means of a classic ultrasonic emitter/receiver 10 and a data processing unit 20 as shown in FIG. 1. The intensity of the echographical image at current point M will be referred to as I(M).

In so doing, a sequence of echographical images of medium B can be obtained, the $n+1^{th}$ image $I_{n+1}(M)$ acquired at $t+(n+1)/f_r$ being separated from the $n^{th}$ image $I_n(M)$ acquired at $t+n/f_r$ by a time interval of $1/f_r$.

After being acquired, the various images are digitalised and stored in memory 30 of FIG. 1.

The next steps of the method leading to the determination of the tissue motion vector will now only make use of said stored digitalised images and digital further processing so as to simulate a Tissue Doppler Imaging method applied to the digitalised images of the medium.

In a first step, 2D images are digitally built up through cross sectional planes, such as plane P of FIG. 2, in order to determine the components of the motion vector V in said plane P. The cross section of the volume of medium B is referred to as C.

Figure 3:
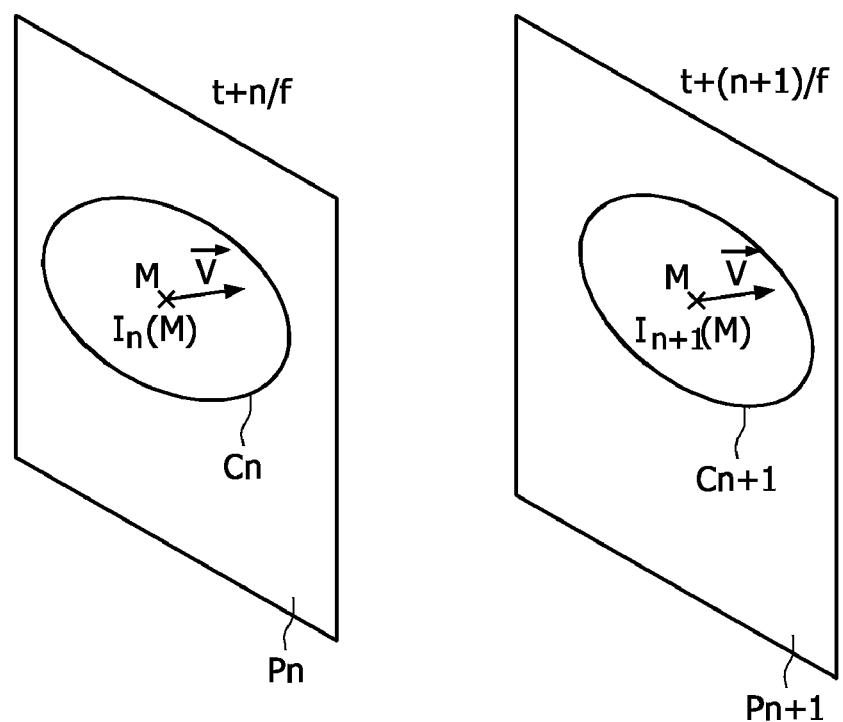
FIG. 3 shows cross sectional planes of the volume of FIG. 2 for two successive images.

In FIG. 3 are shown cross sectional planes $P_n$ and $P_{n+1}$ associated with cross sectional plane P for two successive echographical images recorded respectively at time $t+n/f_r$ and time $t+(n+1)/f_r$. During the time interval $1/f_r$, the image contour C has moved from $C_n$ to $C_{n+1}$ and the image intensity at point M has changed from $I_n(M)$ to $I_{n+1}(M)$.

Figure 4:
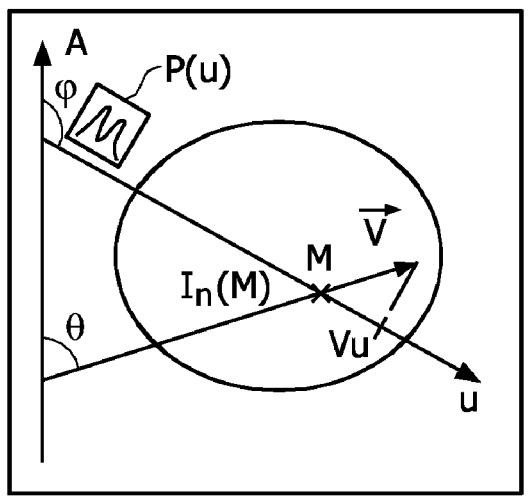
FIG. 4 is a front view of plane $P_n$ shown in FIG. 3.

FIG. 4 shows a front view of plane $P_n$ defining the parameters that will now be used to explain the further steps of the method of determining the component of motion vector V in plane P. As can be seen in FIG. 4, said component is defined by its magnitude V and by its direction θ relative to a given axis A in plane $P_n$. The purpose of the method is to determine the two parameters V and θ.

Figure 5A:
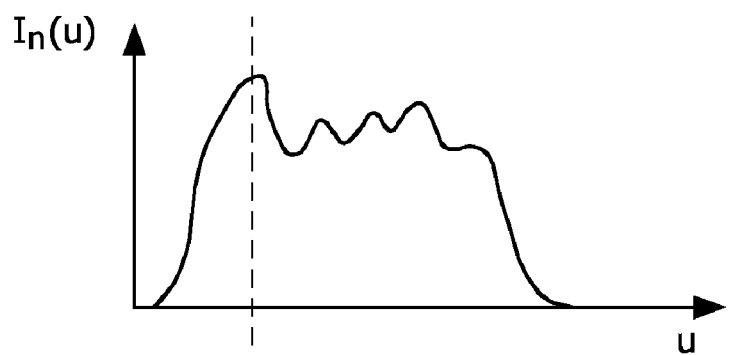
FIGS. 5a and 5b represent echographical signals along the u-axis of FIG. 4 for two successive echographical images.
Figure 5B:
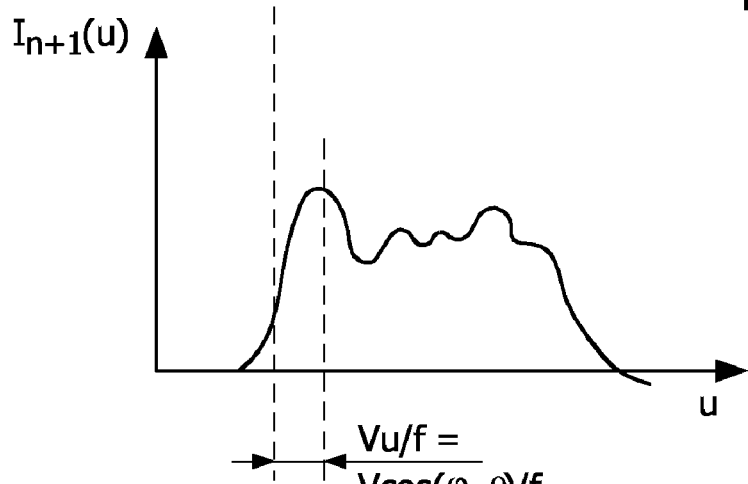

FIG. 5a gives the variations $I_n(u)$ of the echographical image through contour $C_n$ along the direction u defined by the angle ϕ with said A axis. FIG. 5b is analogous to FIG. 5a, but relates to the image $I_{n+1}(u)$ recorded after a period of time equal to $1/f_r$.

As shown in FIG. 5b, the image $I_{n+1}(u)$ has roughly the same shape as that of the image $I_n(u)$, but is shifted by a displacement equal to $\Delta u = V_u/f_r = V\cos(\phi-\theta)/f_r$.

As stated before, this displacement Δu is measured by using a simulation of a Tissue Doppler Imaging method. To this end, a digital pseudo echographical pulse p(u) is needed to simulate the ultrasonic pulse used in this method.

A digital pseudo echographical signal $S_n(u)$ for each value n is reconstructed by effecting the convolution product $p(u) \times I_n(u)$ as shown at reference 40 in FIG. 1:

$$S_n(u) = p(u) \times I_n(u)$$

The $S_n(u)$ signals are then processed according to the Tissue Doppler Imaging method. It is just repeated here that this process is performed by applying to $S_n(u)$ a Quadrature Band Pass (QBP) filter 50, leading to a complex signal $\hat{S}_n(u)$ proportional to $e^{-j2\pi f u}$:

$$\hat{S}_n(u) \approx e^{-j2\pi f u}$$

where f is a spatial frequency equal to the ratio of the ultrasonic frequency to the velocity of the ultrasonic wave in the medium.

Accordingly, $\hat{S}_{n+1}(u)$ is given by:

$$\hat{S}_{n+1}(u) \approx e^{-j2\pi f(u+\Delta u)}$$

Therefore, the product of a complex signal $\hat{S}_n(u)$ and the conjugate of the following one, i.e: $\hat{S}_{n+1}(u)$, is proportional to $e^{j2\pi f \Delta u}$:

$$\hat{S}_n(u)\hat{S}^*_{n+1}(u) \approx e^{j2\pi f \Delta u}$$

By performing an average over n, the following equation is obtained:

$$2\pi f \Delta u = 4\pi f V \cos(\phi-\theta)/f_r = \text{Arg}\hat{S}_n(u)\hat{S}^*_{n+1}(u)$$

It is thus possible to measure at block 60 of FIG. 1 an estimate $<V_u> = <V\cos(\phi-\theta)>$ for the product $V\cos(\phi-\theta)$ from the pseudo echographical signals $S_n(u)$ obtained by the convolution operation of the intensity $I_n(u)$ with the pulse p(u) by averaging the preceding formula over n:

$$4\pi f <V\cos(\phi-\theta)>/f_r = 4\pi f <V_u>/f_r = \text{Arg}(1/N)\Sigma_n \hat{S}_n(u)\hat{S}^*_{n+1}(u)$$

Figure 6:
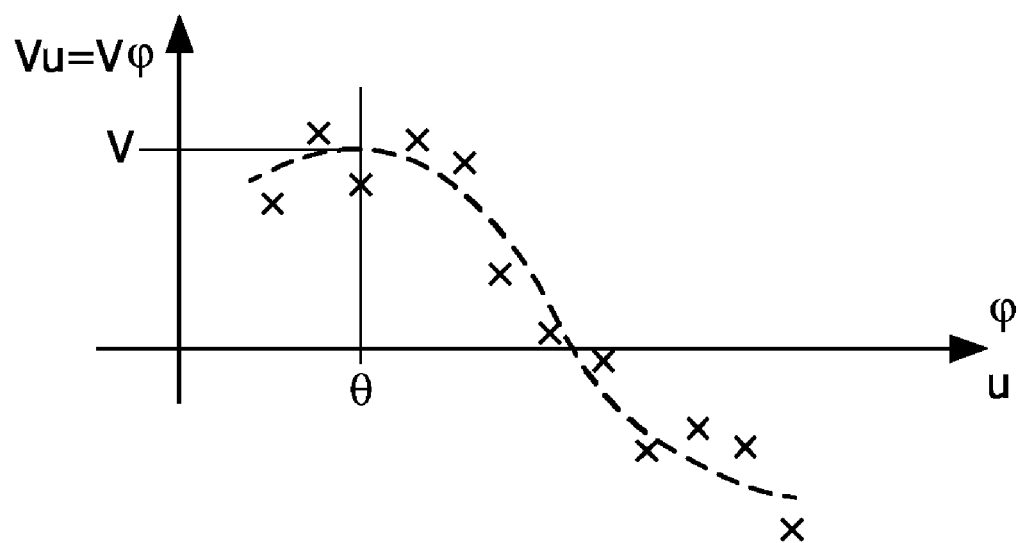
FIG. 6 is a diagram showing how the magnitude and the direction of the motion vector component are extracted.

The so measured values of $V_u$, which can also be written as $V_\phi$, obtained for various values of angle ϕ, every 5° for example, may be plotted as a function of ϕ, as shown in FIG. 6. A best fit method, such as that known as the Newton-Raphson method, applied at block 70 of FIG. 1 leads to the determination of the magnitude V and the direction θ of the motion vector of point M in the cross sectional plane P.

Figure 7:
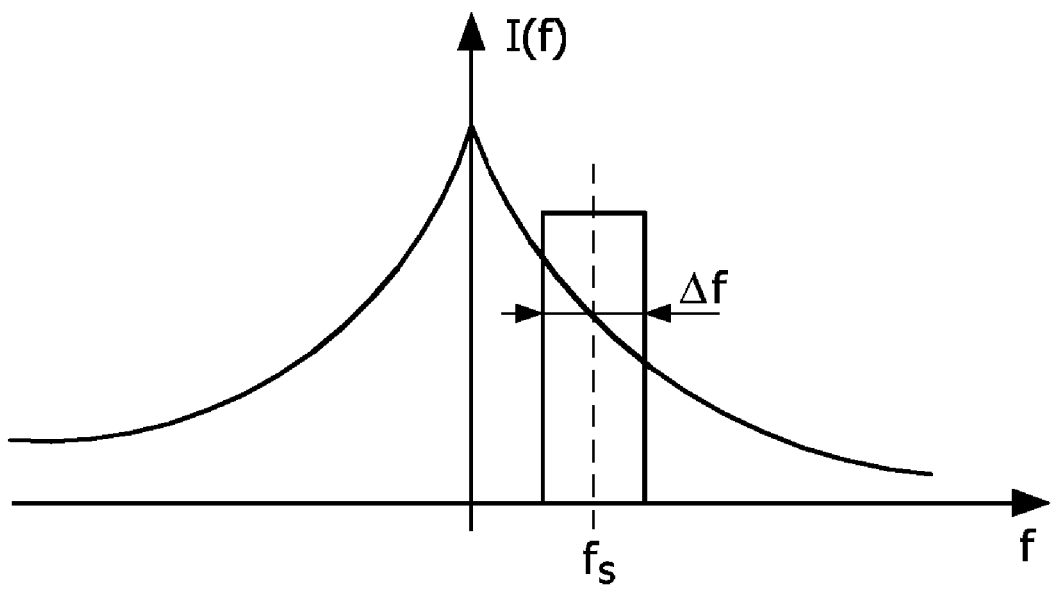
FIG. 7 is a diagram showing the frequency spectrum of the echographical images.

The pulse p(u) can be defined from FIG. 7, which represents the frequency spectrum I(f) of the intensity of the echographical images. This Figure shows a mean frequency f, and a frequency window centered about said mean frequency $f_s$ with a bandwidth of Δf. This frequency window can be taken as the frequency spectrum of pulse p(u), said pulse being obtained by a Fourier transform of said frequency window.

It should be noted that a narrow bandwidth Δf will result in a high accuracy in the determination of the motion vector parameters V and θ but a low spatial resolution, and vice versa.

After the components of the motion vector in plane P have been determined by application of the method which has just been described, it is possible to determine the overall components of said motion vector V by performing the same method in another plane, namely perpendicular to said plane P.

The invention advantageously applies to transverse motion imaging, which cannot be achieved by means of the usual Tissue Doppler Imaging. To this end, the motion vector determined by use of the method and the device according to the invention is merely projected in the corresponding direction. It is thus possible to visualize the motion of cardiac walls away from each other instead of their stretching motion. Then, a color coding may be carried out, the color blue coding motions towards the left and the color red those towards the right.

The invention claimed is:

1. A method of determining a motion vector of tissues in a biological medium, said method comprising the steps of:
   acquiring a sequence of echographical images at a given repetition rate,
   digitalising said echographical images and storing the so-digitalised images,
   defining a digital pseudo echographical pulse,
   effecting in a plurality of directions a convolution of said digital pseudo echographical pulse with said digitalised images and deducing therefrom at each point of said medium a plurality of pseudo echographical signals associated with said plurality of directions,
   determining an estimate over said plurality of directions of a phase shift between two successive pseudo echographical signals and deducing therefrom the magnitude and the direction of said motion vector.

2. A method as claimed in claim 1, wherein said determination is obtained from the determination of the motion vector components in two different planes.

3. A method as claimed in claim 1, wherein said digital pseudo echographical pulse is defined as a Fourier transform of a frequency window centered about the mean frequency of said pseudo echographical signals.

4. A method as claimed in claim 1, wherein the echographical images are cardiac wall images and the determining includes determining cardiac wall motion.

5. A device for determining a motion vector of tissues in a biological medium, said device comprising:

means for acquiring a sequence of echographical images at a given repetition rate, means for digitalising said echographical images and storing the so-digitalised images, means for effecting in a plurality of directions a convolution of a digital pseudo echographical pulse with said digitalised images and means for deducing therefrom at each point of said medium a plurality of pseudo echographical signals associated with said plurality of directions, means for determining an estimate over said plurality of directions of a phase shift between two successive pseudo echographical signals and deducing therefrom the magnitude and the direction of said motion vector.

6. A device as claimed in claim 5, wherein said means for deducing comprise a Quadrature Band Pass filter.

7. A device as claimed in claim 5, wherein said means for determining are capable of determining the motion vector components in two different planes.

8. A device as claimed in claim 5, wherein said digital pseudo echographical pulse is defined as a Fourier transform of a frequency window centered about the mean frequency of said pseudo echographical signals.

9. A device as claimed in claim 5, wherein the echographical images are cardiac wall images and the means for determining determines cardiac wall motion.

* * * * *